(12) United States Patent
McGrath et al.

(10) Patent No.: US 7,678,367 B2
(45) Date of Patent: *Mar. 16, 2010

(54) METHOD FOR REDUCING ODOR USING METAL-MODIFIED PARTICLES

(75) Inventors: Kevin P. McGrath, Alpharetta, GA (US); Bao Trong Do, Decatur, GA (US); John Gavin MacDonald, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1876 days.

This patent is subject to a terminal disclaimer.

(21) Appl. No.: 10/686,939

(22) Filed: Oct. 16, 2003

(65) Prior Publication Data
US 2005/0084464 A1    Apr. 21, 2005

(51) Int. Cl.
| | |
|---|---|
| A01N 59/06 | (2006.01) |
| A61K 9/14 | (2006.01) |
| A61K 33/06 | (2006.01) |
| A61Q 15/00 | (2006.01) |
| A61F 5/00 | (2006.01) |
| B32B 5/00 | (2006.01) |

(52) U.S. Cl. .................. 424/65; 424/489; 424/641; 424/682; 424/724; 424/600; 424/443; 428/98

(58) Field of Classification Search ............... 424/76.1, 424/489, 635, 641, 646, 691, 724, 65, 682, 424/443, 600; 428/98
See application file for complete search history.

(56) References Cited

U.S. PATENT DOCUMENTS

| | | |
|---|---|---|
| 2,015,864 A | 10/1935 | Müller et al. |
| 2,593,146 A | 4/1952 | Howard |
| 3,266,973 A | 8/1966 | Crowley |
| 3,338,992 A | 8/1967 | Kinney |
| 3,341,394 A | 9/1967 | Kinney |
| 3,381,688 A | 5/1968 | Satas |
| 3,494,821 A | 2/1970 | Evans |
| 3,502,538 A | 3/1970 | Petersen |
| 3,502,763 A | 3/1970 | Hartmann |
| 3,507,269 A | 4/1970 | Berry |
| 3,542,615 A | 11/1970 | Dobo et al. |
| 3,615,478 A | 10/1971 | Hoshino et al. |
| 3,692,618 A | 9/1972 | Dorschner et al. |
| 3,794,497 A | 2/1974 | Pratt et al. |
| 3,802,817 A | 4/1974 | Matsuki et al. |
| 3,836,633 A | 9/1974 | Beschke |
| 3,849,241 A | 11/1974 | Butin et al. |
| 3,919,437 A | 11/1975 | Brown et al. |
| 3,960,494 A | 6/1976 | Verma et al. |
| 3,971,665 A | 7/1976 | Suzuki et al. |
| 4,006,030 A | 2/1977 | Yoshida et al. |
| 4,041,203 A | 8/1977 | Brock et al. |
| 4,078,029 A | 3/1978 | Yoshida et al. |
| 4,100,324 A | 7/1978 | Anderson et al. |
| 4,101,638 A | 7/1978 | Inoue et al. |
| 4,144,370 A | 3/1979 | Boulton |
| 4,172,781 A | 10/1979 | Walk et al. |
| 4,297,233 A | 10/1981 | Gualandi |
| RE30,797 E | 11/1981 | Davis |
| RE30,803 E | 11/1981 | Davis |
| 4,313,820 A | 2/1982 | Farha, Jr. et al. |
| 4,340,563 A | 7/1982 | Appel et al. |
| 4,375,448 A | 3/1983 | Appel et al. |
| 4,407,960 A | 10/1983 | Tratnyek |
| 4,451,388 A | 5/1984 | Payne |
| 4,467,012 A | 8/1984 | Pedersen et al. |
| 4,469,746 A | 9/1984 | Weisman et al. |
| 4,488,969 A | 12/1984 | Hou |
| 4,494,278 A | 1/1985 | Kroyer et al. |
| 4,494,629 A | 1/1985 | Raeburn |
| 4,517,308 A | 5/1985 | Ehlenz et al. |
| 4,522,203 A | 6/1985 | Mays |
| 4,525,410 A | 6/1985 | Hagiwara et al. |
| 4,575,556 A | 3/1986 | Byrne et al. |
| 4,604,313 A | 8/1986 | McFarland et al. |
| 4,640,810 A | 2/1987 | Laursen et al. |
| 4,643,801 A | 2/1987 | Johnson |

(Continued)

FOREIGN PATENT DOCUMENTS

EP    0103214 B1    3/1984

(Continued)

OTHER PUBLICATIONS

Article—*Saponins and Sapogenins. VIII. Surface Films of Echinocystic Acid and Derivatives*, C. R. Noller, J. Am. Chem. Soc., vol. 60, 1938, 3 pages.

(Continued)

*Primary Examiner*—Johann R Richter
*Assistant Examiner*—James H. Alstrum-Acevedo
(74) *Attorney, Agent, or Firm*—Dority & Manning, P.A.

(57) ABSTRACT

A method for reducing odor is provided. In one embodiment, the method comprises forming a coordination complex between particles having a positive zeta potential and a transition metal. The method further comprises contacting the coordination complex with an odorous compound, the transition metal providing one or more active sites for capturing the odorous compound. For example, in one embodiment, the particles are formed from alumina-coated silica. In addition, the coordination complex may be formed using a bifunctional chelating agent.

39 Claims, No Drawings

U.S. PATENT DOCUMENTS

| | | |
|---|---|---|
| 4,655,757 A | 4/1987 | McFarland et al. |
| 4,701,218 A | 10/1987 | Barker et al. |
| 4,715,983 A | 12/1987 | Ota et al. |
| 4,725,415 A | 2/1988 | Kidd |
| 4,734,324 A | 3/1988 | Hill |
| RE32,649 E | 4/1988 | Brandt et al. |
| 4,775,585 A | 10/1988 | Hagiwara |
| 4,780,448 A | 10/1988 | Broecker et al. |
| 4,781,858 A | 11/1988 | Mizukami et al. |
| 4,783,220 A | 11/1988 | Gamble et al. |
| 4,798,603 A | 1/1989 | Meyer et al. |
| 4,802,473 A | 2/1989 | Hubbard et al. |
| 4,818,464 A | 4/1989 | Lau |
| 4,823,404 A | 4/1989 | Morell et al. |
| 4,823,803 A | 4/1989 | Nakamura |
| 4,904,304 A | 2/1990 | Watanabe et al. |
| 4,969,457 A | 11/1990 | Hubbard et al. |
| 4,978,615 A | 12/1990 | Aoyama et al. |
| 4,988,505 A | 1/1991 | Watanabe et al. |
| 5,000,746 A | 3/1991 | Meiss |
| 5,020,533 A | 6/1991 | Hubbard et al. |
| 5,057,302 A | 10/1991 | Johnson et al. |
| 5,064,473 A | 11/1991 | Kubo et al. |
| 5,064,599 A | 11/1991 | Ando et al. |
| 5,100,581 A | 3/1992 | Watanabe et al. |
| 5,100,702 A | 3/1992 | Maeda et al. |
| 5,102,592 A | 4/1992 | McCauley et al. |
| 5,108,739 A | 4/1992 | Kurihara et al. |
| 5,120,693 A | 6/1992 | Connolly et al. |
| 5,122,418 A | 6/1992 | Nakane et al. |
| 5,133,803 A | 7/1992 | Moffatt |
| 5,145,518 A | 9/1992 | Winnik et al. |
| 5,145,727 A | 9/1992 | Potts et al. |
| 5,169,706 A | 12/1992 | Collier, IV et al. |
| 5,178,931 A | 1/1993 | Perkins et al. |
| 5,183,656 A | 2/1993 | Uesaka et al. |
| 5,188,885 A | 2/1993 | Timmons et al. |
| 5,196,177 A | 3/1993 | Watanabe et al. |
| 5,204,429 A | 4/1993 | Kaminsky et al. |
| 5,209,998 A | 5/1993 | Kavassalis et al. |
| 5,220,000 A | 6/1993 | Theodoropulos |
| 5,221,497 A | 6/1993 | Watanabe et al. |
| 5,225,374 A | 7/1993 | Fare et al. |
| 5,230,953 A | 7/1993 | Tsugeno et al. |
| 5,238,518 A | 8/1993 | Okubi et al. |
| 5,245,117 A | 9/1993 | Withers et al. |
| 5,266,289 A | 11/1993 | Tsugeno et al. |
| 5,284,703 A | 2/1994 | Everhart et al. |
| 5,292,868 A | 3/1994 | Subramanian |
| 5,294,717 A | 3/1994 | Theodoropulos |
| 5,300,365 A | 4/1994 | Ogale |
| 5,314,855 A | 5/1994 | Thorpe et al. |
| 5,322,061 A | 6/1994 | Brunson |
| 5,332,432 A | 7/1994 | Okubi et al. |
| 5,338,713 A | 8/1994 | Takagi et al. |
| 5,342,876 A | 8/1994 | Abe et al. |
| 5,350,624 A | 9/1994 | Georger et al. |
| 5,366,947 A | 11/1994 | Müller et al. |
| 5,382,400 A | 1/1995 | Pike et al. |
| 5,383,450 A | 1/1995 | Hubbard et al. |
| 5,397,667 A | 3/1995 | Law et al. |
| 5,407,442 A | 4/1995 | Karapasha |
| 5,407,600 A | 4/1995 | Ando et al. |
| 5,420,090 A | 5/1995 | Spencer et al. |
| 5,427,844 A | 6/1995 | Murai et al. |
| 5,429,628 A | 7/1995 | Trinh et al. |
| 5,432,000 A | 7/1995 | Young, Sr. et al. |
| 5,451,450 A | 9/1995 | Erderly et al. |
| 5,458,864 A | 10/1995 | Tsugeno et al. |
| 5,472,775 A | 12/1995 | Obijeski et al. |
| 5,480,636 A | 1/1996 | Maruo et al. |
| 5,486,356 A * | 1/1996 | Yim .......................... 424/76.1 |
| 5,487,938 A | 1/1996 | Spencer et al. |
| 5,488,126 A | 1/1996 | Subramanian et al. |
| 5,527,171 A | 6/1996 | Soerensen |
| 5,538,548 A | 7/1996 | Yamazaki |
| 5,539,124 A | 7/1996 | Etherton et al. |
| 5,540,916 A | 7/1996 | Parks |
| 5,547,607 A | 8/1996 | Ando et al. |
| 5,553,608 A | 9/1996 | Reese et al. |
| 5,554,775 A | 9/1996 | Krishnamurti et al. |
| 5,580,655 A | 12/1996 | El-Shall et al. |
| 5,583,219 A | 12/1996 | Subramanian et al. |
| 5,591,797 A | 1/1997 | Barthel et al. |
| 5,597,512 A | 1/1997 | Watanabe et al. |
| 5,616,315 A | 4/1997 | Masterman et al. |
| 5,661,198 A | 8/1997 | Inatani et al. |
| 5,663,224 A | 9/1997 | Emmons et al. |
| 5,679,138 A | 10/1997 | Bishop et al. |
| 5,679,724 A | 10/1997 | Sacripante et al. |
| 5,695,868 A | 12/1997 | McCormack |
| 5,733,272 A | 3/1998 | Brunner et al. |
| 5,747,003 A | 5/1998 | Mohnot et al. |
| 5,773,227 A | 6/1998 | Kuhn et al. |
| 5,795,985 A | 8/1998 | Hüsler et al. |
| 5,813,398 A | 9/1998 | Baird et al. |
| 5,817,300 A | 10/1998 | Cook et al. |
| 5,837,352 A | 11/1998 | English et al. |
| 5,843,509 A | 12/1998 | Calvo Salve et al. |
| 5,855,788 A | 1/1999 | Everhart et al. |
| 5,858,503 A | 1/1999 | Everhart et al. |
| 5,861,144 A | 1/1999 | Peterson et al. |
| 5,871,872 A | 2/1999 | Matijevic et al. |
| 5,874,067 A | 2/1999 | Lucas et al. |
| 5,880,176 A | 3/1999 | Kamoto et al. |
| 5,880,309 A | 3/1999 | Suzuki et al. |
| 5,882,638 A | 3/1999 | Dodd et al. |
| 5,885,599 A | 3/1999 | Peterson et al. |
| 5,897,541 A | 4/1999 | Uitenbroek et al. |
| 5,902,226 A | 5/1999 | Tasaki et al. |
| 5,905,101 A | 5/1999 | Fujiki et al. |
| 5,916,596 A | 6/1999 | Desai et al. |
| 5,948,398 A | 9/1999 | Hanamoto et al. |
| 5,948,483 A | 9/1999 | Kim et al. |
| 5,962,566 A | 10/1999 | Grandfils et al. |
| 5,964,926 A | 10/1999 | Cohen |
| 5,972,389 A | 10/1999 | Shell et al. |
| 5,985,229 A | 11/1999 | Yamada et al. |
| 5,989,510 A | 11/1999 | Abe et al. |
| 5,989,515 A | 11/1999 | Watanabe et al. |
| 5,998,222 A | 12/1999 | Weimer |
| 6,004,625 A | 12/1999 | Ohshima |
| 6,007,592 A | 12/1999 | Kasai et al. |
| 6,024,786 A | 2/2000 | Gore |
| 6,045,900 A | 4/2000 | Haffner et al. |
| 6,047,413 A | 4/2000 | Welchel et al. |
| 6,060,410 A | 5/2000 | Gillberg-LaForce et al. |
| 6,073,771 A | 6/2000 | Pressley et al. |
| 6,075,179 A | 6/2000 | McCormack et al. |
| 6,096,299 A | 8/2000 | Guarracino et al. |
| 6,111,163 A | 8/2000 | McCormack et al. |
| 6,172,173 B1 | 1/2001 | Spencer et al. |
| 6,177,608 B1 | 1/2001 | Weinstrauch |
| 6,190,814 B1 | 2/2001 | Law et al. |
| 6,193,844 B1 | 2/2001 | McLaughlin et al. |
| 6,200,555 B1 | 3/2001 | Nishijima et al. |
| 6,210,625 B1 | 4/2001 | Matsushita et al. |
| 6,225,524 B1 | 5/2001 | Guarracino et al. |
| 6,238,767 B1 | 5/2001 | McCormack et al. |
| 6,254,894 B1 | 7/2001 | Denkewicz, Jr. et al. |
| 6,264,615 B1 | 7/2001 | Diamond et al. |
| 6,277,346 B1 | 8/2001 | Murasawa et al. |
| 6,277,489 B1 | 8/2001 | Abbott et al. |
| 6,277,772 B1 | 8/2001 | Gancet et al. |

| | | |
|---|---|---|
| 6,291,535 B1 | 9/2001 | Watanabe et al. |
| 6,294,222 B1 | 9/2001 | Cohen et al. |
| 6,299,867 B1 | 10/2001 | Aoyagi et al. |
| 6,309,736 B1 | 10/2001 | McCormack et al. |
| 6,315,864 B2 | 11/2001 | Anderson et al. |
| 6,334,988 B1 | 1/2002 | Gallis et al. |
| 6,344,218 B1 | 2/2002 | Dodd et al. |
| 6,344,272 B1 | 2/2002 | Oldenburg et al. |
| 6,358,537 B1 | 3/2002 | Hoshino et al. |
| 6,358,909 B1 | 3/2002 | Ochomogo et al. |
| 6,361,780 B1 | 3/2002 | Ley et al. |
| 6,361,944 B1 | 3/2002 | Mirkin et al. |
| 6,369,290 B1 | 4/2002 | Glaug et al. |
| 6,376,741 B1 | 4/2002 | Guarracino et al. |
| 6,387,495 B1 | 5/2002 | Reeves et al. |
| 6,398,827 B1 | 6/2002 | Ota et al. |
| 6,410,616 B1 * | 6/2002 | Harada et al. ............... 523/337 |
| 6,410,765 B1 | 6/2002 | Wellinghoff et al. |
| 6,425,530 B1 | 7/2002 | Coakley |
| 6,427,693 B1 | 8/2002 | Blackstock et al. |
| 6,428,814 B1 | 8/2002 | Bosch et al. |
| 6,432,872 B1 | 8/2002 | Tsushio et al. |
| 6,433,243 B1 | 8/2002 | Woltman et al. |
| 6,440,187 B1 | 8/2002 | Kasai et al. |
| 6,460,989 B1 | 10/2002 | Yano et al. |
| 6,461,735 B1 | 10/2002 | Furuya et al. |
| 6,467,897 B1 | 10/2002 | Wu et al. |
| 6,468,500 B1 | 10/2002 | Sakaguchi et al. |
| 6,475,601 B1 | 11/2002 | Sakaki et al. |
| 6,479,150 B1 | 11/2002 | Liu et al. |
| 6,491,790 B1 | 12/2002 | Proverb et al. |
| 6,498,000 B2 | 12/2002 | Murasawa et al. |
| 6,517,199 B1 | 2/2003 | Tomioka et al. |
| 6,531,704 B2 | 3/2003 | Yadav et al. |
| 6,536,890 B1 | 3/2003 | Kato et al. |
| 6,548,264 B1 | 4/2003 | Tan et al. |
| 6,551,457 B2 | 4/2003 | Westman et al. |
| 6,562,441 B1 | 5/2003 | Maeda et al. |
| 6,575,383 B2 | 6/2003 | Dobler et al. |
| 6,578,521 B2 | 6/2003 | Raymond et al. |
| 6,589,562 B1 | 7/2003 | Shefer et al. |
| 6,607,711 B2 | 8/2003 | Pedersen |
| 6,623,848 B2 | 9/2003 | Brehm et al. |
| 6,638,918 B2 | 10/2003 | Davison et al. |
| 6,639,004 B2 | 10/2003 | Falat et al. |
| 6,645,569 B2 | 11/2003 | Cramer et al. |
| 6,680,279 B2 | 1/2004 | Cai et al. |
| 6,693,071 B2 | 2/2004 | Ghosh et al. |
| 6,830,694 B2 * | 12/2004 | Schiestel et al. ............ 210/660 |
| 7,008,979 B2 | 3/2006 | Schottman et al. |
| 2001/0000889 A1 | 5/2001 | Yadav et al. |
| 2001/0023338 A1 | 9/2001 | Guarracino et al. |
| 2001/0031248 A1 | 10/2001 | Hall-Puzio et al. |
| 2001/0056246 A1 | 12/2001 | Rodriguez-Fernandez |
| 2002/0005145 A1 | 1/2002 | Sherman |
| 2002/0066542 A1 | 6/2002 | Jakob et al. |
| 2002/0091071 A1 | 7/2002 | Fischer et al. |
| 2002/0106466 A1 | 8/2002 | Hausmann et al. |
| 2002/0110686 A1 | 8/2002 | Dugan |
| 2002/0128336 A1 | 9/2002 | Kolb et al. |
| 2002/0142937 A1 | 10/2002 | Carter et al. |
| 2002/0149656 A1 | 10/2002 | Nohr et al. |
| 2002/0150678 A1 | 10/2002 | Cramer et al. |
| 2002/0176982 A1 | 11/2002 | Rohrbaugh et al. |
| 2002/0177621 A1 | 11/2002 | Hanada |
| 2002/0182102 A1 | 12/2002 | Fontenot et al. |
| 2003/0013369 A1 | 1/2003 | Soane et al. |
| 2003/0021983 A1 | 1/2003 | Nohr et al. |
| 2003/0050211 A1 | 3/2003 | Hage et al. |
| 2003/0056648 A1 | 3/2003 | Fornai et al. |
| 2003/0070782 A1 | 4/2003 | Proverb et al. |
| 2003/0082237 A1 | 5/2003 | Cha et al. |
| 2003/0099718 A1 | 5/2003 | Burrell et al. |
| 2003/0100842 A1 | 5/2003 | Rosenberg et al. |
| 2003/0147956 A1 | 8/2003 | Shefer et al. |
| 2003/0147966 A1 | 8/2003 | Franzen et al. |
| 2003/0181540 A1 | 9/2003 | Quellet et al. |
| 2003/0203009 A1 | 10/2003 | MacDonald |
| 2003/0235605 A1 | 12/2003 | Lelah et al. |
| 2004/0033269 A1 | 2/2004 | Hei et al. |
| 2004/0034157 A1 | 2/2004 | Ghosh et al. |
| 2004/0043688 A1 | 3/2004 | Soerens et al. |
| 2005/0084438 A1 * | 4/2005 | Do et al. ............... 423/244.02 |
| 2005/0181067 A1 | 8/2005 | Yokoyama et al. |

FOREIGN PATENT DOCUMENTS

| | | |
|---|---|---|
| EP | 0232141 A1 | 8/1987 |
| EP | 0251783 B1 | 1/1988 |
| EP | 0282287 B2 | 9/1988 |
| EP | 0339461 B1 | 11/1989 |
| EP | 0348978 A2 | 1/1990 |
| EP | 0376448 B1 | 7/1990 |
| EP | 0389015 A2 | 9/1990 |
| EP | 0389015 A3 | 9/1990 |
| EP | 0389023 A2 | 9/1990 |
| EP | 0389023 A3 | 9/1990 |
| EP | 0483500 A1 | 5/1992 |
| EP | 0510619 A1 | 10/1992 |
| EP | 0749295 B1 | 12/1996 |
| EP | 0972563 A1 | 1/2000 |
| EP | 1034800 A1 | 9/2000 |
| EP | 1157672 A1 | 11/2001 |
| EP | 1162172 A1 | 12/2001 |
| EP | 1188854 A1 | 3/2002 |
| EP | 1214878 A1 | 6/2002 |
| EP | 1216675 A1 | 6/2002 |
| EP | 1298071 A1 | 4/2003 |
| EP | 1315526 B1 | 6/2003 |
| EP | 1053788 B1 | 10/2003 |
| JP | 62149322 | 7/1987 |
| JP | 3221142 | 9/1991 |
| WO | WO 8902698 A1 | 4/1989 |
| WO | WO 9111977 A1 | 8/1991 |
| WO | WO 9112029 A1 | 8/1991 |
| WO | WO 9112030 A1 | 8/1991 |
| WO | WO 9619346 A2 | 6/1996 |
| WO | WO 9619346 A3 | 6/1996 |
| WO | WO 9725076 A1 | 7/1997 |
| WO | WO 9820915 A1 | 5/1998 |
| WO | WO9820915 A1 | 5/1998 |
| WO | WO 9826808 A2 | 6/1998 |
| WO | WO 9826808 A3 | 6/1998 |
| WO | WO 99/30752 * | 6/1999 |
| WO | WO9947252 A3 | 9/1999 |
| WO | WO 0003797 A1 | 1/2000 |
| WO | WO 0013764 A1 | 3/2000 |
| WO | WO 0029036 A2 | 3/2000 |
| WO | WO 0029036 A3 | 3/2000 |
| WO | WO 0059555 A1 | 10/2000 |
| WO | WO 0076558 A1 | 12/2000 |
| WO | WO0106054 A1 | 1/2001 |
| WO | WO 03025067 A1 | 3/2002 |
| WO | WO 0226272 A1 | 4/2002 |
| WO | WO 0249559 A2 | 6/2002 |
| WO | WO02055115 A1 | 7/2002 |
| WO | WO 02062881 A2 | 8/2002 |
| WO | WO 02064877 A2 | 8/2002 |
| WO | WO 02064877 A3 | 8/2002 |
| WO | WO 02083297 A1 | 10/2002 |
| WO | WO 02084017 A1 | 10/2002 |
| WO | WO 02094329 A1 | 11/2002 |
| WO | WO 02095112 A1 | 11/2002 |
| WO | WO03000979 A2 | 1/2003 |
| WO | WO 03032959 A1 | 4/2003 |
| WO | WO 03088931 | 10/2003 |

| WO | WO 03092885 A1 | 11/2003 |
| WO | WO 2004000986 A1 | 12/2003 |
| WO | WO 2004/060378 A2 | 7/2004 |

OTHER PUBLICATIONS

Article—*Synthesis of porous Silica with help from cyclodextrin aggregates*, Markus Antonietti, Max-Planck-Institut für Kolloid-und, Germany, 1 page.

Article—*Immobilization of $(n\text{-}Bu_4N)_4W_{10}O_{32}$ on Mesoporous MCM-41 and Amorphous Silicas for Photocatalytic Oxidation of Cycloalkanes with Molecular Oxygen*, Andrea Maldotti, Alessandra Molinari, Graziano Varani, Maurizio Lenarda, Loretta Storaro, Franca Bigi, Raimondo Maggi, Alessandro Mazzacani, and Giovanni Sartori, Journal of Catalysis, vol. 209, 2002, pp. 210-216.

Article—*Fe-MCM-41 for Selective Epoxidation of Styrene with Hydrogen Peroxide*, Qinghong Zhang, Ye Wang, Satoko Itsuki, Tetsuya Shishido, and Katsuomi Takehira, The Chemical Society of Japan, Chemistry Letters 2001, pp. 946-947.

Article—*Mesoporous Sieves with Unified Hybrid Inorganic/Organic Frameworks*, Brian J. Melde, Brian T. Holland, Christopher F. Blanford, and Andreas Stein, Chem. Mater., vol. 11, No. 11, 1999, pp. 3302-3308.

Article—*From Cyclodextrin Assemblies to Porous Materials by Silica Templating*, Sebastian Polarz, Bernd Smarsly, Lyudmila Bronstein, and Markus Antonietti, Angew. Chem. Int., vol. 40, No. 23, 2001, pp. 4417-4421.

Paper—*Uniform Deposition of Ultrathin Polymer Films on the Surfaces of $Al_2O_3$ Nanoparticles by a Plasma Treatment*, Donglu Shi, S. X. Wang, Wim J. van Ooij, L. M. Wang, Jiangang Zhao, and Zhou Yu, University of Cincinnati and University of Michigan, Jun. 2000, pp. 1-15.

Article—*Development of novel dye-doped silica nanoparticles for biomarker application*, Swadeshmukul Santa, Kemin Wang, Rovelyn Tapec, and Weihong Tan, Journal of Biomedical Optics, vol. 6, No. 2, Apr. 2001, pp. 160-166.

Article—*Nanoparticles based on polyelectrolyte complexes: effect of structure and net charge on the sorption capability for solved organic molecules*, H.-M. Buchhammer, G. Petzold, and K. Lunkwitz, Colloid Polym. Sci., vVol. 278, 2000, pp. 841-847.

Article—*Adsorption of Gases in Multimolecular Layers*, Stephen Brunauer, P.H. Emmett, and Edward Teller, The Journal of the American Chemical Society, vol. 60, Feb. 1938, pp. 309-319.

Article—*Study of the urea thermal decomposition (pyrolysis) reaction and importance to cyanuric acid production*, Peter M. Schaber, James Colson, Steven Higgins, Ed Dietz, Daniel Thielen, Bill Anspach, and Jonathan Brauer, American Laboratory, Aug. 1999, pp. 13-21.

Article—*The Colloid Chemistry of Silica*, American Chemical Society 200th National Meeting, Aug. 26-31, 1990, pp. 22-23 and pp. 52-59.

Article—*Structure and properties of silica nanoclusters at high temperatures*, I. V. Schweigert, K. E. J. Lehtinen, M. J. Carrier, and M. R. Zachariah, The American Physical Society, Physical Review B, vol. 65. No. 235410, pp. 1-9.

Article—*Grafting of Poly(ethylenimine) onto Mesylated Cellulose Acetate, Poly(methyl methacrylate) and Poly (vinyl chloride)*, Christopher J. Biermann and Ramani Narayan; Carbohydrate Polymers, vol. 12, 1990, pp. 323-327.

Abstract of Article—*Non-hydrothermal synthesis of copper-,-zinc- and copper-zinc hydrosilicates*, T. M. Yurieva, G. N. Kustova, T. P. Minyukova, E. K. Poels, A. Bliek, M. P. Demeshkina, L. M. Plyasova, T. A. Krieger, and V. I. Zaikovskii, Materials Research Innovations, vol. 5, No. 1, Jun. 2001, pp. 3-11.

Pocket Guide to Digital Printing, Frank Cost, Delmar Publishers, Albany, NY, ISBN 0- 8273-7592-1, pp. 144-145.

Product Information Sheets on Snowtex®, 6 pages.

Abstract of Japanese Patent No. 5106199, Apr. 27, 1993.

Abstract of Japanese Patent No. 9143872, Jun. 3, 1997.

Article—*Applicability of a SPME method for the Rapid Determination of VOCs*, Alexandre Béné, Jean-Luc Luisier, and Antoine Fornage, Chimia, vol. 56, No. 6, 2002, pp. 289-291.

Article—*Characterisation of novel modified active carbons and marine algal biomass for the selective adsorption of lead*, D.J. Malik, V. Strelko, Jr., M. Streat, and A.M. Puziy; Water Research, vol. 36, 2002, pp. 1527-1538.

Article—*Significance of Ammonia in the Genesis of Gastric Epithelial Lesions Induced by Helicobacter pylori: An in vitro Study with Different Bacterial Strains and Urea Concentrations*, P. Sommi, V. Ricci, R. Fiocca, M. Romano, K.J. Ivey, E. Cova, E. Solcia, and U. Ventura, Digestion, vol. 57, 1996, pp. 299-304.

Article—*Ammonia vapour in the mouth as a diagnostic marker for Helicobacter pylori infection: preliminary "proof of principle" pharmacological investigations*, C. D. R. Dunn, M. Black, D. C. Cowell, C. Penault, N. M. Ratcliffe, R. Spence, and C. Teare, British Journal of Biomedical Science, vol. 58, 2001, pp. 66-76.

Article—*Purification and Characterization of Urease from Helicobacter pylori*, Bruce E. Dunn, Gail P. Campbell, Guillermo I. Perez-Perez, and Martin J. Blaser, The Journal of Biological Chemistry, vol. 265, No. 16, Jun. 5, 1990, pp. 9464-1990.

Article—*Validation of $^{13}$C-Urea Breath Test for the Diagnosis of Helicobacter Pylori Infection in the Singapore Population*, T. S. Chua, K. M. Fock, E. K. Teo, T. M. Ng, Singapore Medical Journal, vol. 43, No. 8, 2002, pp. 408-411.

Article—*Significance of ammonia produced by Helicobacter pylori*, Shigeji Ito, Yoshihiro Kohli, Takuji Kato, Yoshimichi Abe, and Takashi Ueda, European Journal of Gastroenterology & Hepatology, vol. 6, No. 2, 1994, pp. 167-174.

Article—*Spectrophotometric Assay of Thiols*, Peter C. Jocelyn, Methods in Enzymology, vol. 142, 1987, pp. 44-67.

Article—*Adsorption of Dyes on Nanosize Modified Silica Particles*, Guangwei Wu, Athanasia Koliadima, Yie-Shein Her, and Egon Matijevic, Journal of Colloid and Interface Sciences, vol. 195, 1997, pp. 222-228.

Article—*Adsorption of Proteins and Antibiotics on Porous Alumina Membranes*, Yi Hua Ma, Aseem Bansal, and William M. Clark, Fundamentals of Adsorption, vol. 80, 1992, pp. 389-396.

Abstract of Japanese Patent No. 7256025, Oct. 9, 1995.

Article—*Immunization of mice with peptomers covalently couopled to aluminum oxide nanoparticles*, Andreas Frey, Nicholas Mantis, Pamela A. Kozlowski, Alison J. Quayle, Adriana Bajardi, Juana J. Perdomo, Frank A. Robey, and Marian R. Neutra, Vaccine, vol. 17, 1999, pp. 3007-3019.

PCT Search Report for PCT/US03/39737, Jun. 18, 2004.

Abstract of SU834073, May 30, 1981.

PCT Search Report and Written Opinion for PCT/US2004/011596, Aug. 30, 2004.

PCT Search Report and Written Opinion for PCT/US2004/016933, Nov. 2, 2004.

Abstract of Japanese Patent No. JP1262868, Oct. 19, 1989.

Abstract of Japanese Patent No. JP2157039, Jun. 15, 1990.

Abstract of Japanese Patent No. JP3195562, Aug. 27, 1991.

Abstract of Japanese Patent No. JP4335141, Nov. 24, 1992.

Abstract of Japanese Patent No. JP5261246, Oct. 12, 1993.

Abstract of Japanese Patent No. JP6285140, Oct. 11, 1994.

Abstract of Japanese Patent No. JP63072337, Apr. 2, 1988.

Abstract of Japanese Patent No. JP8152409, Jun. 11, 1996.

U.S. Appl. No. 10/723,761, filed Nov. 26, 2004, Quincy, III, et al., Odor Control in Personal Care Products.

U.S. Appl. No. 10/955,316, filed Sep. 30, 2004, MacDonald, et al., Odor-Reducing Quinone Compounds.

Abstract of Japanese Patent No. JP04225767, Sep. 10, 1992.

Abstract of Japanese Patent No. JP05098185, Apr. 20, 1993.

Lye, et al., U.S. Appl. No. 10/325,474, filed Dec. 20, 2002, Delivery System For Functional Compounds.

Quincy, III, et al., U.S. Appl. No. 10/328,730, filed Dec. 23, 2002, Odor Control Composition.

MacDonald, et al., U.S. Appl. No. 10/686,933, filed Oct. 16, 2003, Method For Reducing Odor Using Colloidal Nanoparticles.

Wu, et al., U.S. Appl. No. 10/686,937, filed Oct. 16, 2003, Method For Reducing Odor Using Coordinated Polydentate Compounds.

Do, et al., U.S. Appl. No. 10/686,938, filed Oct. 16, 2003, Method For Reducing Odor Using Metal-Modified Silica Particles.

MacDonald, et al., U.S. Appl. No. 10/686,687, filed Oct. 16, 2003, Durable Charged Particle Coatings And Materials.

Urlaub, et al., U.S. Appl. No. 10/687,004, filed Oct. 16, 2003, High Surface Area Material Blends For Odor, Reduction, Articles Utilizing Such Blends And Methods Of Using Same.

MacDonald, et al., U.S. Appl. No. 10/687,269, filed Oct. 16, 2003, Odor Controlling Article Including A Visual Indicating Device For Monitoring Odor Absorption.

MacDonald, et al., U.S. Appl. No. 10/687,270, filed Oct. 16, 2003, Visual Indicating Device For Bad Breath.

Boga, et al., U.S. Appl. No. 10/687,327, filed Oct. 16, 2003, Method And Device For Detecting Ammonia Odors And Helicobacter Pylori Urease Infection.

Fish, et al., U.S. Appl. No. 10/687,425, filed Oct. 16, 2003, Odor Absorbing Extrudates.

* cited by examiner

METHOD FOR REDUCING ODOR USING METAL-MODIFIED PARTICLES

BACKGROUND OF THE INVENTION

Odor control additives have been conventionally incorporated into substrates for a variety of reasons. For instance, U.S. Pat. No. 6,225,524 to Guarracino, et al. describes a substrate having an odor control composition that includes an absorbent gelling material and silica. Likewise, U.S. Pat. No. 6,376,741 to Guarracino, et al. describes a substrate having an odor control composition that includes silica and a zeolite (i.e., crystalline aluminosilicate). For instance, one type of silica said to be preferred in Guarracino, et al. ('524 patent) is amorphous silica having a particle size of 4-12 microns and a pore volume of 1-2 g/ml. Another type of preferred silica is said to be a silica gel having a medium pore diameter of from 90 to 110 angstroms, a surface area of from 250 $m^2/g$ to 350 $m^2/g$, and an average particle size of from 63 to 200 microns. Unfortunately, conventional odor control compositions, such as described above, have proven ineffective in obtaining the full level of odor control desired in many applications.

As such, a need exists for an odor control composition that may exhibit improved odor control properties, particularly when applied to a substrate.

SUMMARY OF THE INVENTION

In accordance with one embodiment of the present invention, a method for reducing odor is disclosed. The method comprises modifying particles having a positive zeta potential with a transition metal. The method further comprises contacting the modified particles with an odorous compound, the transition metal providing one or more active sites for capturing the odorous compound. For example, in one embodiment, the particles are formed from alumina-coated silica. In addition, the modified particles may be formed using a bifunctional chelating agent.

In accordance with another embodiment of the present invention, an odor control composition is disclosed that comprises particles coated with alumina that are modified with a transition metal. The particles have a positive zeta potential, and the transition metal provides one or more active sites for capturing an odorous compound. In accordance with still another embodiment of the present invention, a substrate for reducing odor is disclosed. The substrate is applied with particles coated with alumina that are modified with a transition metal.

Other features and aspects of the present invention are discussed in greater detail below.

DETAILED DESCRIPTION OF REPRESENTATIVE EMBODIMENTS

Definitions

As used herein, a "coordinate bond" refers to a shared pair of electrons between two atoms, wherein one atom supplies both electrons to the pair.

As used herein, a "covalent bond" refers to a shared pair of electrons between two atoms, wherein each atom supplies one electron to the pair.

As used herein, the term "zeta potential" refers to the potential gradient that arises across an interface. Zeta potential measurements may be taken using, for instance, a Zetapals instrument available from the Brookhaven Instrument Corporation of Holtsville, N.Y. For example, zeta potential measurements may be conducted by adding one to three drops of a sample into a cuvet containing 1 millimolar KCl solution, using the instrument's default functions preset for aqueous solutions.

As used herein, an "absorbent article" refers to any article capable of absorbing water or other fluids. Examples of some absorbent articles include, but are not limited to, personal care absorbent articles, such as diapers, training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Materials and processes suitable for forming such absorbent articles are well known to those skilled in the art.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblowing" refers to a process in which fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonding" refers to a process in which small diameter substantially continuous fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. Nos. 4,340,563 to Appel, et al., 3,692,618 to Dorschner, et al., 3,802,817 to Matsuki, et al., 3,338,992 to Kinney, 3,341,394 to Kinney, 3,502,763 to Hartman, 3,502,538 to Levy, 3,542,615 to Dobo, et al., and 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

Detailed Description

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

In general, the present invention is directed to particles configured to reduce various types of odors. The particles may be formed from a variety of materials, including, but not limited to, silica, alumina, zirconia, magnesium oxide, titanium dioxide, iron oxide, zinc oxide, copper oxide, organic compounds such as polystyrene, and combinations thereof. The particles may possess various forms, shapes, and sizes depending upon the desired result. For instance, the particles may be in the shape of a sphere, crystal, rod, disk, tube, string, etc. The average size of the particles is generally less than about 500 microns, in some embodiments less than about 100 microns, in some embodiments less than about 100 nanometers, in some embodiments from about 1 to about 50 nanometers, in some embodiments from about 2 to about 50 nanometers, and in some embodiments, from about 4 to about 20 nanometers. As used herein, the average size of a particle refers to its average length, width, height, and/or diameter.

The particles may have a surface area of from about 50 square meters per gram ($m^2/g$) to about 1000 $m^2/g$, in some embodiments from about 100 $m^2/g$ to about 600 $m^2/g$, and in some embodiments, from about 180 $m^2/g$ to about 240 $m^2/g$. Surface area may be determined by the physical gas adsorption (B.E.T.) method of Bruanauer, Emmet, and Teller, Journal of American Chemical Society, Vol. 60, 1938, p. 309, with nitrogen as the adsorption gas. If desired, the particles may also be relatively nonporous or solid. That is, the particles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. Without intending to be limited by theory, it is believed that particles having such a small size and high surface area may improve the adsorption capability for many odorous compounds. Moreover, it is believed that the solid nature, i.e., low pore volume, of the particles may enhance the uniformity and stability of the particles, without sacrificing their odor adsorption characteristics.

Regardless of the material used to form the particles, it is generally desired that the particles possess a positive "zeta potential." The particles of the present invention may have a zeta potential of greater than about +20 millivolts (mV), in some embodiments greater than about +30 mV, and in some embodiments, greater than about +40 mV. By possessing a positive surface charge, the particles are well suited for being affixed to substrates that carry a negative surface charge through ionic attraction. Depending upon the difference in charge between the particles of the present invention and the surface of a substrate, the bond in some applications may be relatively permanent and substantive. Consequently, the particles of the present invention may be affixed to various substrates without the use of chemical binders or other attachment structures.

A positive zeta potential may be imparted to the particles of the present invention in a variety of different ways. In one embodiment, the particles are formed entirely from a positively charged material. For example, alumina particles may be used for odor reduction in accordance with the present invention. Some suitable alumina particles are described in U.S. Pat. No. 5,407,600 to Ando, et al., which is incorporated herein in its entirety by reference thereto for all purposes. Further, examples of commercially available alumina particles include, for instance, Aluminasol 100, Aluminasol 200, and Aluminasol 520, which are available from Nissan Chemical Industries Ltd. Alternatively, the positive zeta potential may be imparted by a continuous or discontinuous coating present on the surface of a core material. In some instances, these particles may actually possess a better stability over various pH ranges than particles formed entirely from positively charged materials. In one particular embodiment, for example, the particles are formed from silica particles coated with alumina. A commercially available example of such alumina-coated silica particles is Snowtex-AK, which is available from Nissan Chemical of Houston, Tex.

Silica particles possess units that may or may not be joined together. Whether or not such units are joined generally depends on the conditions of polymerization. For instance, the acidification of a silicate solution may yield $Si(OH)_4$. If the pH of this solution is reduced below 7 or if a salt is added, then the units may tend to fuse together in chains and form a "gel." On the other hand, if the pH is kept at a neutral pH or above 7, the units may tend to separate and gradually grow to form a "sol." Silica particles may generally be formed according to any of a variety of techniques well known in the art, such as dialysis, electrodialysis, peptization, acid neutralization, and ion exchange. Some examples of such techniques are described, for instance, in U.S. Pat. Nos. 5,100,581 to Watanabe, et al.; 5,196,177 to Watanabe, et al.; 5,230,953 to Tsugeno, et al. and 5,985,229 to Yamada, et al., which are incorporated herein in their entirety by reference thereto for all purposes.

For exemplary purposes only, one embodiment of an ion-exchange technique for forming an alumina-coated silica sol will now be described in more detail. Initially, an alkali metal silicate is provided that has a molar ratio of silicon ($SiO_2$) to alkali metals ($M_2O$) of from about 0.5 to about 4.5. For instance, sodium water glass may be utilized that has a molar ratio of from about 2 to about 4. An aqueous solution of the alkali metal silicate is obtained by dissolving it in water at a concentration of, for instance, from about 2 wt. % to about 6 wt. %. The alkali metal silicate-containing aqueous solution may then be contacted with one or more ion-exchange resins. For instance, the solution may first be contacted with a strong-acid to ion-exchange all the metal ions in the aqueous solution. Examples of such strong acids include, but are not limited to, hydrochloric acid, nitric acid, sulfuric acid, and so forth. The contact may be accomplished by passing the aqueous solution through a column filled with the strong acid at a temperature of from about 0° C. to about 60° C., and in some embodiments, from about 5° C. to about 50° C. After passing through the column, the resulting silicic acid-containing aqueous solution may have a pH value of from about 2 to about 4. If desired, another strong acid may be added to the silicic acid-containing aqueous solution to convert the impurity metal components into dissociated ions. This additional strong acid may decrease the pH value of the resulting solution to less than about 2, and in some embodiments, from about 0.5 to about 1.8.

The metal ions and the anions from the strong acid may be removed from the solution by consecutive application of a strong acid (i.e., cation-exchange resin) and strong base (anion-exchange resin). Examples of suitable strong bases include, but are not limited to, sodium hydroxide, potassium hydroxide, and so forth. As a result of this consecutive application, the silicic acid-containing aqueous solution may have a pH value of from about 2 to about 5. This acidic aqueous solution may then be contacted with one or more additional strong bases to stabilize the solution at a pH value of from about 7 to about 9.

The stabilized silicic acid-containing aqueous solution is then fed to a container in which the liquid temperature is maintained at from about 70° C. to about 100° C. This process results in an increase in concentration of the silica to from about 30 wt. % to about 50 wt. %. The stable aqueous silica sol may then be consecutively contacted with a strong acid and strong base, such as described above, so that the resulting aqueous silica sol is substantially free from polyvalent metal oxides, other than silica. Finally, ammonia may be added to the aqueous sol to further increase its pH value to from about 8 to about 10.5, thereby forming a stable aqueous silica sol having a silica concentration of from about 30 wt. % to about 50 wt. %, a mean particle size of from about 10 to about 30 nanometers, and that is substantially free from any polyvalent metal oxides, other than silica.

To coat the silica sol with alumina, it is mixed with an aqueous solution of from about 0.2 wt. % to about 10 wt. % of a basic metal salt based on the amount of SiO$_2$ in the silica sol. Examples of some suitable basic metal salts that may be used include, but are not limited to, aluminum chloride, aluminum acetate, aluminum nitrate, aluminum formate, and so forth. The resulting aqueous sol contains colloidal silica particles coated with ions of aluminum. In some instances, other materials may be coated onto the silica instead of, or in conjunction with, the alumina. For example, zirconia may be coated onto the silica sol by using a zirconium-based salt.

The aqueous sol is then adjusted to pH of from about 4 to about 7 with an alkaline aqueous solution to give a positively charged silica sol. The alkaline aqueous solution may include, for instance, alkali metal hydroxides (such as lithium, sodium, potassium, rubidium, and cesium hydroxides), ammonium hydroxide, water-soluble quaternary ammonium hydroxides, guanidine hydroxide, water-soluble alkylamines (such as ethylamine, isopropylamine, and n-propylamine), water-soluble alkanolamines (such as monoethanolamine and triethanolamine), benzylamine, and piperidine. The alkaline substance may be present in the solution at a concentration of from about 0.5 wt. % to about 30 wt %. If desired, the resulting alkaline particles may be subjected to one or more additional consecutive applications of negatively charged silica particles and a basic metal salt to form a more stable positively charged silica sol having the desired particle size.

In accordance with the present invention, the particles are also modified with one or more transition metals. Examples of some suitable transition metals that maybe used in the present invention include, but are not limited to, scandium, titanium, vanadium, chromium, manganese, iron, cobalt, nickel, copper, zinc, silver, gold, and so forth. Single metallic, as well as dimeric, trinuclear, and cluster systems may be used. Without being limited by theory, it is believed that the transition metal provides one or more active sites for capturing and/or neutralizing an odorous compound. Further, the presence of the transition metal is also believed to help improve the Lewis acidity of the silica, thus rendering it more receptive to free electron pairs of many odorous compounds.

The transition metal may be incorporated onto the surface of the particles in a variety of ways. For instance, the particles may simply be mixed with a solution containing the appropriate transition metal in the form of a salt, such as those containing a copper ion ($Cu^{+2}$), silver ion ($Ag^+$), gold ion ($Au^+$ and $Au^{+3}$), iron (II) ion ($Fe^{+2}$), iron (III) ion ($Fe^{+3}$), and so forth. Such solutions are generally made by dissolving a metallic compound in a solvent resulting in free metal ions in the solution. However, because the particles and metal ions both possess a positive charge, the metal ions are not typically drawn to the particles based on electric potential.

Thus, a chelating agent is used to form a coordination complex with the transition metal. To ensure that this coordinated transition metal is adhered to the surface of the particles, e.g., to the alumina, it is normally desired that the chelating agent is "bifunctional." That is, the chelating agent is capable of forming both a coordination complex with metal ions and also a bond with the particles. This ensures strong adherance of the transition metal to the particles, and reduces the likelihood that any of the transition metal will be free during use (e.g., after washing). Such bifunctional chelating agents generally contain one or more chelating moieties for binding to the metal ion and reactive moieties that bond to the surface of particles, such as alumina. The chelating and reactive moieties may include, for instance, hydroxyl, carboxy, imino, amino (e.g. primary amines, secondary amines, or tertiary amines), carbonyl, etc. The present inventors have discovered that moieties, such as described above, may form a relatively strong bond (e.g., covalent bond) with an alumina surface.

In one embodiment, for example, a bifunctional chelating agent containing two or more iminodiacetic acid groups may be utilized. Iminodiacetic acid groups generally have the following structure:

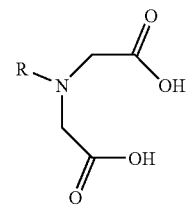

One example of such a bifunctional chelating agent is ethylenediaminetetraacetic acid (EDTA), which has the following general structure:

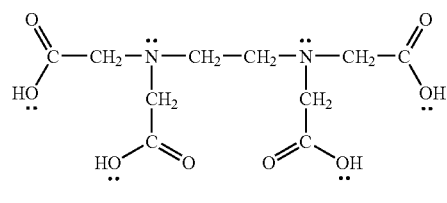

ethylenediaminetetraacetic acid (EDTA)

EDTA is capable of tightly coordinating transition metals and irreversibly adsorbing onto the surface of particles, such as alumina. Due to the strength of the EDTA-alumina interaction, the transition metal remains bound during use. Other examples of similar iminodiacetic acid-based chelating agents include, but are not limited to, butylenediaminetetraacetic acid, (1,2-cyclohexylenediaminetetraacetic acid (CyDTA), diethylenetriaminepentaacetic acid, ethylenediaminetetrapropionic acid, (hydroxyethyl)ethylenediaminetriacetic acid (HEDTA), N,N,N',N'-ethylenediaminetetra (methylenephosphonic) acid (EDTMP), triethylenetetraminehexaacetic acid (TTHA), 1,3-diamino-2-hydroxypropane-N, N,N',N'-tetraacetic acid (DHPTA), methyliminodiacetic acid, propylenediaminetetraacetic acid, and so forth.

In another embodiment, aromatic polyols may be utilized. Some examples of such aromatic polyols include, but are not limited to, 1,2-benzenediol (catechol); 3-methyl-1,2-benzenediol; 4-methyl-1,2-benzenediol; 3-ethyl-1,2-benzenediol; 4-ethyl-1,2-benzenediol; 3-tert-butyl-1,2-benzenediol; 4-tert-butyl-1,2-benzenediol; 3-tert-octyl-1,2-benzenediol;

4-tert-octyl-1,2-benzenediol; 3-methoxy-1,2-benzenediol; 4-methoxy-1,2-benzenediol; 3-ethoxy-1,2-benzenediol; 4-ethoxy-1,2-benzenediol; 1,2,3-benzenetriol (pyrogallol); 1,2,4-benzenetriol (hydroquinol); 1,2,3,5-benzenetetrol; 1,2,4,5-benzenetetrol; 1,2,3,4-benzenetetrol (apionol); 1,2-naphthalenediol; 2,3-naphthalenediol; 1,2,3-naphthalenetriol; 1,2,4-naphthalenetriol; 1,2,5-naphthalenetriol; 1,2,6-naphthalenetriol; 1,2,7-naphthalenetriol; 2,3,6-naphthalenetriol; 1,2,4,5-naphthalenetetrol; and 1,2,4,7-naphthalenetetrol. Preferred aromatic polyols are catechol and pyrogallol. For instance, the structure of a typical catechol is provided below.

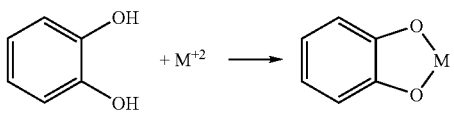

As shown, the catechol has two hydroxyl functional groups that act in concert to coordinate a transition metal ion "M". Because the catechol only has the ability to coordinate one metal per molecule, it is typically desired to use a chelating agent having two or more catechol functional groups, such as hematoxylin (a dye containing two catechol moieties), so that a bond with the particles is also formed.

Still another class of suitable chelating agents includes anthraquinones having the following general structure:

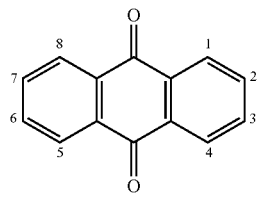

The numbers indicate the substitution positions of the anthraquinone structure. For instance, the table set forth below provides some substituents that might occur at positions 1, 4, 5, or 8 on the anthraquinone structure. Of course, other substituents may also be present.

| Name | Substituent at Position 1, 4, 5, or 8 | Other Substituents |
|---|---|---|
| CI Acid Black 48 | $NH_2$ | $SO_3Na$ |
| CI Acid Blue 25 | $NH_2$ | $SO_3Na$ |
| CI Acid Blue 40 | $NH_2$ | $SO_3Na$ |
| CI Acid Blue 41 | $NH_2$ | $SO_3Na$ |
| CI Acid Blue 45 | OH, $NH_2$ | $SO_3Na$ |
| CI Acid Blue 129 | $NH_2$ | $SO_3Na$ |
| CI Acid Green 25 | NH(Aramid ("Ar")) | $SO_3Na$ |
| CI Acid Green 27 | NHAr | $SO_3Na$ |
| CI Acid Green 41 | OH, NHAr | $SO_3Na$ |
| CI Mordant Red 11 (Alizarin) | OH | |
| CI Mordant Black 13 (Alizarin Blue Black B) | OH, NHAr | $SO_3Na$ |
| Alizarin Complexone (Aldrich 12,765-5) | OH | |
| CI Mordant Red 3 (Alizarin Red S) | OH | $SO_3Na$ |
| CI Natural Red 4 (Carminic Acid) | OH | COOH |
| CI Disperse Blue 1 | NH2 | |
| CI Disperse Blue 3 | NH(alkyl) | |
| CI Disperse Blue 14 | $NHCH_3$ | |
| Emodin (6-methyl-1,3,8-trihydroxy anthraquinone) | OH | |
| Nuclear Fast Red (Heliofast Rubine BBL) | OH, $NH_2$ | $SO_3Na$ |
| CI Natural Red 16 (Purpurin) | OH | |
| CI Natural Red 8 | OH | |
| Quinalizarin | OH | |
| Quinizarin | OH | |
| CI Reactive Blue 2 | $NH_2$, NHAr | $SO_3Na$ |
| Solvent Green 3 | NHAr | |

The functional groups present on the anthraquinone structure may act in concert with the central carbonyl moiety to coordinate transition metal ions. In most embodiments of the present invention, di-substituted anthraquinones are utilized to facilitate the coordination of metal ions and bonding to the surface of the particles.

Besides anthraquinones, other dyes may also possess chelating capabilities. For example, dyes containing salicylate (1, R=OH), salicamide (1, R=$NH_2$, NHAr, NHAlk), or BON acid (3-hydroxy-2-naphthoic acid) (2, R=OH) or a nitrogenous BON acid derivative (2, R=$NH_2$, NHAr, NHAlk) moiety as shown below may also be used in accordance with the present invention. These dyes often fall into the Colour Index Mordant application class.

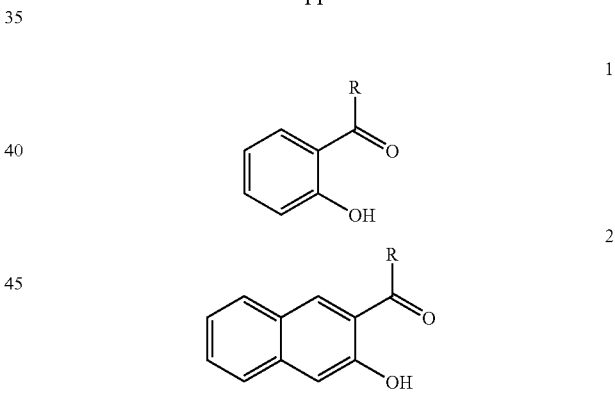

Dyes based upon chromotropic acid 3 may also be used. Azo dyes are formed when chromotropic acid is reacted with a diazonium salt.

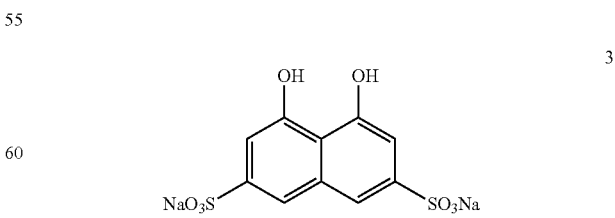

Dyes containing acetoacetanilide moieties 4 may also be used. Azo dyes couple to acetoacetanilide beta to the two carboxyl groups. An example is Cl Acid Yellow 99, 5.

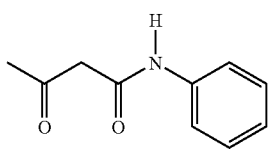

Acetoacetanilide

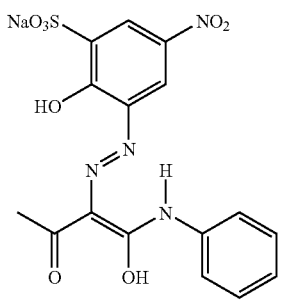

CI Acid Yellow 99

Naphthoquinone (6) type structures are also useful as chelating agents:

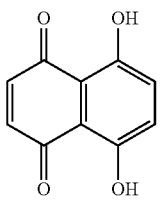

Further, there are several dyes that are useful for the coloration of anodized aluminum, including Cl Mordant Red 7 (Eriochrome Red B), 7, that may also be used. It is believed that the geometry of the five membered pyrazolone ring oxygen atom brings it into the correct position with the beta-naphthol group for complexation with alumina. Thus, the following structure may be considered a functional equivalent to a carbonyl-hydroxy moiety. The structure also contains an iminalogous amide moiety, which is functionally equivalent to a vinalogous amide.

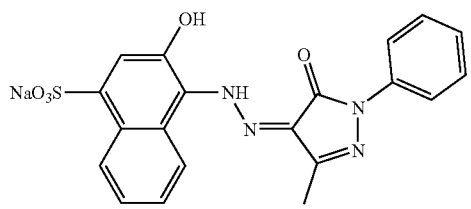

Many of the bifunctional chelating agents described above possess two or more of the same functional group. However, in some embodiments, the bifunctionality of the chelating agent may instead be imparted by different functionalities. For example, as mentioned above, EDTA possesses two iminodiacetic acid functionalities. In some embodiments, however, a compound may be utilized that contains an iminodiacetic acid functionality and another functionality, such as a catechol. In one embodiment, for example, a catechol is provided that has the following structure:

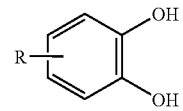

where, R is a primary amine, such as 3-hydroxytyramine, 3,4-dihydroxybenzylamine, L-DOPA, etc. This catechol structure may then be reacted with an acetic acid compound, such as iodoacetic acid, bromoacetic acid, or chloroacetic acid, to form a catechol compound containing an iminodiacetic acid group as the "R" moiety.

It should be understood that the chelating agents referenced above are merely exemplary, and that other bifunctional chelating agents known in the art may also be used in the present invention. For example, various other bifunctional chelating agents that may be used in the present invention are described in U.S. Pat. Nos. 4,575,556 to Byrne, et al.; 5,057,302 to Johnson, et al.; 5,225,374 to Johnson, et al., 5,220,000 to Theodoropulos; 5,294,717 to Theodoropulos; 5,292,868 to Subramanian; 5,488,126 to Johnson, et al.; 5,583,219 to Subramanian, et al.; 5,773,227 to Kuhn, et al., which are incorporated herein in their entirety by reference thereto for all purposes.

The transition metal present on the surface of the particle of the present invention is believed to provide one or more active sites for capturing and/or neutralizing odorous compounds. The active sites may be free, or simply be weak enough so that they are replaced by an odorous molecule when contacted therewith. In addition, the particles still have the large surface area that is useful in absorbing other odorous compounds. For example, the particles of the present invention may be used in various applications to remove odorous compounds, such as mercaptans (e.g., ethyl mercaptan), ammonia, amines (e.g., trimethylamine (TMA), triethylamine (TEA), etc.), sulfides (e.g., hydrogen sulfide, dimethyl disulfide (DMDS), etc.), ketones (e.g., 2-butanone, 2-pentanone, 4-heptanone, etc.) carboxylic acids (e.g., isovaleric acid, acetic acid, propionic acid, etc.), aldehydes, terpenoids, hexanol, heptanal, pyridine, and combinations thereof.

If desired, more than one type of transition metal may be bound to a particle. This has an advantage in that certain metals may be better at removing specific odorous compounds than other metals. Likewise, different types of modified particles may be used in combination for effective removal of various odorous compounds. In one embodiment, for instance, copper-modified particles are used in combination with manganese-modified particles. By using two different modified particles in combination, numerous odorous compounds may be more effectively removed. For example, the copper-modified particle may be more effective in removing sulfur and amine odors, while the manganese-modified particle may be more effective in removing carboxylic acids.

The ratio of the bifunctional chelating agent to the transition metal may be selectively varied to achieve the desired results. In most embodiments, for example, the ratio of the chelating agent to the transition metal is at least about 10:1, in some embodiments at least about 50:1, and in some embodiments, at least about 100:1. Similarly, the ratio of the transition metal to the particles may also be varied. In most embodiments, for example, the ratio of the transition metal to the particles is also at least about 10:1, in some embodiments at least about 50:1, and in some embodiments, at least about 100:1. Generally speaking, the order in which the particles, chelating agent, and transition metal are mixed may be varied as desired. In some instances, the order of mixing may actually affect the characteristics of the modified particles. For instance, if the chelating agent is mixed first with the particles, unwanted precipitation may sometimes occur. Thus, in some embodiments, it may be desired to first mix the chelating agent with the transition metal, and then mix the resulting complex with the particles.

If desired, the modified particles of the present invention may be applied to a substrate. The substrate may provide an increased surface area to facilitate the adsorption of odorous compounds by the particles. In addition, the substrate may also serve other purposes, such as water absorption. Any of a variety of different substrates may be incorporated with the particles in accordance with the present invention. For instance, nonwoven fabrics, woven fabrics, knit fabrics, wet-strength paper, film, foams, etc., may be applied with the particles. When utilized, the nonwoven fabrics may include, but are not limited to, spunbonded webs (apertured or non-apertured), meltblown webs, bonded carded webs, air-laid webs, coform webs, hydraulically entangled webs, and so forth.

In some embodiments, for example, the modified particles may be utilized in a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter (gsm), in some embodiments less than about 80 gsm, in some embodiments less than about 60 grams per square meter, and in some embodiments, from about 10 to about 60 gsm.

Any of a variety of materials can also be used to form the paper web(s) of the product. For example, the material used to make the paper product may include fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-19". Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, and so forth. In addition, in some instances, synthetic fibers can also be utilized. Some suitable synthetic fibers can include, but are not limited to, rayon fibers, ethylene vinyl alcohol copolymer fibers, polyolefin fibers, polyesters, and so forth.

One particular benefit of the present invention is that the modified particles still typically have a zeta potential of greater than about +20 millivolts (mV), in some embodiments greater than about +30 mV, and in some embodiments, greater than about +40 mV. By possessing a positive surface charge, the particles are well suited for being affixed to substrates that carry a negative surface charge through ionic attraction. Cellulosic fibrous materials, for instance, often contain hydroxy and/or carboxyl groups that result in a negative surface charge. Thus, the modified particles of the present invention may form an electrostatic bond with these materials, and thus remain affixed thereto without the need for chemical binders or other attachment structures.

If desired, the substrate may form all or a portion of an absorbent article. In one embodiment, for instance, the absorbent article includes a liquid-transmissive bodyside liner, a liquid-transmissive surge layer below the bodyside liner, a liquid-absorbent core below the surge layer, and a moisture vapor permeable, liquid impermeable outer cover below the absorbent core. A substrate treated with the modified particles of the present invention may be employed as any one or more of the liquid transmissive (non-retentive) and absorbent layers. An absorbent core of the absorbent article, for instance, may be formed from an absorbent nonwoven web that includes a matrix of hydrophilic fibers. In one embodiment, the absorbent web may contain a matrix of cellulosic fluff fibers. One type of fluff that may be used in the present invention is identified with the trade designation CR1654, available from U.S. Alliance, Childersburg, Ala., U.S.A., and is a bleached, highly absorbent sulfate wood pulp containing primarily soft wood fibers. In another embodiment, the absorbent nonwoven web may contain a hydroentangled web. Hydroentangling processes and hydroentangled composite webs containing various combinations of different fibers are known in the art. A typical hydroentangling process utilizes high pressure jet streams of water to entangle fibers and/or filaments to form a highly entangled consolidated fibrous structure, e.g., a nonwoven fabric. Hydroentangled non-woven fabrics of staple length fibers and continuous filaments are disclosed, for example, in U.S. Pat. Nos. 3,494,821 to Evans and 4,144,370 to Bouolton, which are incorporated herein in their entirety by reference thereto for all purposes. Hydroentangled composite nonwoven fabrics of a continuous filament nonwoven web and a pulp layer are disclosed, for example, in U.S. Pat. Nos. 5,284,703 to Everhart, et al. and 6,315,864 to Anderson, et al., which are incorporated herein in their entirety by reference thereto for all purposes.

Another type of suitable absorbent nonwoven web is a coform material, which is typically a blend of cellulose fibers and meltblown fibers. The term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and so forth. Some examples of such coform materials are disclosed in U.S. Pat. Nos. 4,100,324 to Anderson, et al.; 5,284,703 to Everhart, et al.; and 5,350,624 to Georger, et al.; which are incorporated herein in their entirety by reference thereto for all purposes.

If desired, the absorbent nonwoven web may also contain a superabsorbent material. Superabsorbents have the ability to absorb a great amount of fluid in relation to their own weight. Typical superabsorbents used in sanitary napkins may absorb anywhere from about 5 to about 60 times their weight in blood. Superabsorbent materials are produced in a wide variety of forms including, but not limited to, particles, fibers and flakes. Superabsorbents having a high mechanical stability in the swollen state, an ability to rapidly absorb fluid, and those having a strong liquid binding capacity, typically perform well in absorbent articles. Hydroxyfunctional polymers have been found to be good superabsorbents for this application. For example, a hydrogel-forming polymer, such as a partially neutralized cross-linked copolymer of polyacrylic acid and polyvinyl alcohol, may be utilized. After the polymer is formed, it is mixed with about a 1% anhydrous citric acid powder. The citric acid has been found to increase the ability of the superabsorbent to absorb menses and blood. This is particularly beneficial for use in a sanitary napkin or other feminine pads. The finely ground, anhydrous citric acid powder, which is void of water, along with trace amounts of fumed silica, is mixed with the polymer that may have been screened to an appropriate particle size. This mixture may also be formed into a composite or a laminate structure. Such superabsorbents may be obtained from Dow Chemical and Stockhausen, Inc., among others. This superabsorbent is a partially neutralized salt of cross-linked copolymer of polyacrylic acid and polyvinyl alcohol having an absorbency under load value above about 25. Some suitable superabsorbents are described in U.S. Pat. Nos. 4,798,603 to Meyers, et al., Re. 32,649 to Brandt, et al. and 4,467,012 to Pedersen, et al., 4,604,313 and 4,655,757 to McFarland, et al., 6,387,495 to Reeves, et al., as well as in published European Patent Application 0,339,461 to Kellenberger.

As indicated above, the modified particles may also be applied to a liquid transmissive layer of the absorbent article, such as the bodyside liner or surge layer. Such liquid transmissive layers are typically intended to transmit liquid quickly, and thus generally do not retain or absorb significant quantities of aqueous liquid. Materials that transmit liquid in such a manner include, but are not limited to, thermoplastic spunbonded webs, meltblown webs, bonded carded webs, air laid webs, and so forth. A wide variety of thermoplastic materials may be used to construct these non-retentive nonwoven webs, including without limitation polyamides, polyesters, polyolefins, copolymers of ethylene and propylene, copolymers of ethylene or propylene with a $C_4$-$C_{20}$ alpha-olefin, terpolymers of ethylene with propylene and a $C_4$-$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, poly-1-butene, copolymers of poly-1-butene including ethylene-1-butene copolymers, polybutadiene, isobutylene-isoprene copolymers, and combinations of any of the foregoing.

The amount of the modified particles present on the substrate may vary depending on the nature of the substrate and its intended application. In some embodiments, for example, the dry, solids add-on level is from about 0.001% to about 20%, in some embodiments from about 0.01% to about 10%, and in some embodiments, from about 0.1% to about 4%. The "solids add-on level" is determined by subtracting the weight of the untreated substrate from the weight of the treated substrate (after drying), dividing this calculated weight by the weight of the untreated substrate, and then multiplying by 100%. Lower add-on levels may provide optimum absorbency or other characteristics of the substrate, while higher add-on levels may provide optimum odor reduction.

The modified particles may be applied to a substrate using any of a variety of well-known application techniques. Suitable techniques for applying the composition to a substrate include printing, dipping, spraying, melt extruding, solvent coating, powder coating, and so forth. The particles may be incorporated within the matrix of the substrate and/or applied to the surface thereof. For example, in one embodiment, particles are coated onto one or more surfaces of the substrate. When coated onto the substrate, the resulting thickness of the coating may be minimal so that it is almost invisible to the naked eye. For instance, the thickness of the coating may be less than about 2 microns, in some embodiments from about 2 to about 500 nanometers, and in some embodiments, from about 20 to about 200 nanometers.

The percent coverage of the modified particles on the surface may be selected to achieve the desired odor reduction. Typically, the percent coverage is greater than about 50%, in some embodiments greater than about 80%, and in some embodiments, approximately 100% of the area of a given surface. The present inventors have discovered that, even when applied uniformly (e.g., about 100% coverage) onto a surface of the substrate, the resulting substrate may still remain porous. Specifically, without intending to be limited by theory, it is believed that the small size of the particles limits their ability to block the pores of the substrate.

Thus, in some instances, a substrate containing the particle coating may remain porous to provide a variety of benefits. For instance, the porosity of the coated substrate may enable it to still be used in application where liquid permeability is required, such as in absorbent articles. Also, the porosity of the coated substrate allows gaseous odorous compounds to flow therethrough, exposing the underside of the particles (surface of particles facing the substrate) to the odorous compound. In this manner, the entire surface area of the particles is more effectively utilized for reducing odor. In most embodiments, the coated substrate exhibits a porosity such that about 20 cubic feet of air or greater may flow through 1 square foot of the substrate in 1 minute under an air pressure differential of 125 Pascals (0.5 inches of water). In other words, such a substrate is said to have an air permeability of about 20 cubic feet per minute (cfm) or greater. In some embodiments, the air permeability ranges from about 20 cfm to about 500 cfm, in some embodiments from about 50 cfm to about 400 cfm, and in some embodiments, from about 75 cfm to about 300 cfm, under an air pressure differential of 125 Pascals. Air permeability (volumetric air flow per square foot of material under an air pressure differential of 125 Pascals) may be measured in a variety of ways. For example, "Frazier Air Permeability" is determined according to Federal Test Standard 191A, Method 5450 with a Frazier Air Permeability Tester (Frazier Precision Instrument Co., Gaithersburg, Md.), and is reported as an average of 3 sample readings.

The modified particles of the present invention are versatile and may also be used with other types of articles of manufacture. For instance, the modified particles may be used in air filters, such as house filters, vent filters, disposable facemasks, and facemask filters. Exemplary facemasks, for instance, are described and shown, for example, in U.S. Pat. Nos. 4,802,473; 4,969,457; 5,322,061; 5,383,450; 5,553,608; 5,020,533; 5,813,398; and 6,427,693, which are incorporated herein in their entirety by reference thereto for all purposes. In one embodiment, a substrate coated with the modified particles of the present invention may be utilized as a filtration layer of the facemask. Filtration layers, such as meltblown nonwoven webs, spunbond nonwoven webs, and laminates thereof, are well known in the art.

In another embodiment, the modified particles may be applied to walls, wallpaper, glass, toilets, and/or countertops. For instance, the modified particles may be used in a restroom facility. Other uses include, without limitation, refrigerator mats and fabric softener sheets.

The modified particles may also be applied to water treatment systems for removing sulphurous compounds from well water or in toilet tanks to reduce the odors resulting from urine. The modified particles may also be used in liquid detergents and household cleaners to remove odors. In another embodiment, the modified particles are used as aerosol odor neutralizers/deodorants. The modified particles are packaged with a propellant that allows spraying the modified particles into the air for removal of gases and odorous compounds. The modified particles may be used in a household air freshener or be used in combination with a mist emitted from a vaporizer or humidifier.

The effectiveness of the modified particles of the present invention may be measured in a variety of ways. For example, the percent of an odorous compound adsorbed by the modified particles may be determined in accordance with the headspace gas chromatography test set forth herein. In some embodiments, for instance, the modified particles of the present invention are capable of adsorbing at least about 25%, in some embodiments at least about 45%, and in some embodiments, at least about 65% of a particular odorous compound. The effectiveness of the modified particles in removing odors may also be measured in terms of "Relative Adsorption Efficiency", which is also determined using headspace gas chromatography and measured in terms of milligrams of odor adsorbed per gram of modified particle. It should be recognized that the surface chemistry of any one type of modified particle may not be suitable to reduce all types of odors, and that low adsorption of one or more odorous compounds may be compensated by good adsorption of other odorous compounds.

The present invention may be better understood with reference to the following examples.

Test Methods

Quantitative and qualitative tests were used in the Examples. Quantitative odor adsorption was determined in the Examples using a test known as "Headspace Gas Chromatography." Headspace gas chromatography testing was conducted on an Agilent Technologies 5890, Series II gas chromatograph with an Agilent Technology 7694 headspace sampler (Agilent Technologies, Waldbronn, Germany). Helium was used as the carrier gas (injection port pressure: 12.7 psig; headspace vial pressure: 15.8 psig; supply line pressure is at 60 psig). A DB-624 column was used for the odorous compound that had a length of 30 meters and an internal diameter of 0.25 millimeters. Such a column is available from J&W Scientific, Inc. of Folsom, Calif.

The operating parameters used for the headspace gas chromatography are shown below in Table 1:

TABLE 1

| Operating Parameters for the Headspace Gas Chromatography Device. Headspace Parameters | | |
|---|---|---|
| Zone Temps, ° C. | Oven | 37 |
| | Loop | 42 |
| | TR. Line | 47 |

TABLE 1-continued

| Operating Parameters for the Headspace Gas Chromatography Device. Headspace Parameters | | |
|---|---|---|
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing 5 milligrams of the modified particles in a 20-cubic centimeter headspace vial. Using a syringe, an aliquot of the odorous compound was also placed in the vial. Testing was done with 839 micrograms of ethyl mercaptan (1 microliter), 804 micrograms (1 microliter) of isovaleraldehyde, and 726 micrograms (1 microliter) of triethylamine (TEA). Each sample was tested in triplicate. The vial was then sealed with a cap and a septum and placed in the headspace gas chromatography oven at 37° C. After two (2) hours, a hollow needle was inserted through the septum and into the vial. A 1-cubic centimeter sample of the headspace (air inside the vial) was then injected into the gas chromatograph. Initially, a control vial with only the aliquot of odorous compound was tested to define 0% odorous compound adsorption. To calculate the amount of headspace odorous compound removed by the sample, the peak area for the odorous compound from the vial with the sample was compared to the peak area from the odorous compound control vial.

Qualitative odor reduction was also assessed against common odors, such as garlic, cigarette and urine.

EXAMPLE 1

The effectiveness of the modified particles to adsorb odorous compounds was demonstrated. The particles were Snowtex-AK, which are colloidal silica nanoparticles coated with alumina and commercially available from Nissan Chemical America of Houston, Tex. The particles have an average particle size of between 10 to 20 nanometers and a surface area between 180 to 240 square meters per gram.

The particles were modified with a transition metal as follows. Initially, 1 milliliter of a 10-millimolar anthraquinone dye solution (carminic acid, Acid Blue 45, Alizarin Red S, and Acid Green 41 all separately tested) was added to an equal volume of a 10-millimolar of copper chloride ($CuCl_2$). The carminic acid-containing solution, for instance, immediately changed from a medium red color to a deep reddish purple color, indicating the formation of a complex. To this complex was then added 1 millimeter of a 200-micromolar solution of the Snowtex-AK particles (approximately 20 wt. % solids). Thus, the ratio of copper-coordinated dye to the particles was 50:1. The mixture was stirred at room temperature for 20 minutes, and then the solvent was removed under rotary evaporation. The dried particles (approximately 200 milligrams) were split into 2 portions, one of which was washed to remove any unbound dye and/or copper. No dye was observed in the washes. About 60 milligrams of each sample was then placed into a 100-microliter screwtop jar that contained two slices of freshly cut garlic. The caps were screwed shut, and the dried particles and odor were incubated at room temperature for 30 minutes. Qualitative comparison indicated that the samples formed with the dye reduced the odor to a much greater extent than a "no dye" control sample.

The solutions containing the Acid Blue 45 dye were applied to paper towels, polyester/cellulose wetlaid webs, and a polyester/cotton blend (from a t-shirt). The polyester/cotton blend was subjected to 3 washes in hot water/detergent using a commercial washing machine. Three samples of the products were then tested for odor adsorption as described above. For comparative purposes, three samples were also tested that did not contain the dye. The results are shown below in Table 2 in terms of the average percentage of odorous compound removed for the three samples.

TABLE 2

Removal of Odorous Compounds

| Sample | Avg. % Ethyl Mercaptan Removed | Avg. % TEA Removed | Avg. % Isovaleraldehyde Removed |
|---|---|---|---|
| Control | 11.3 (stdev = 3.2) | 15.0 (stdev = 3.0) | 10.3 (stdev = 2.9) |
| Copper/ Snowtex-AK/ Acid Blue 45 | 80.0 (stdev = 3.1) | 61.3 (stdev = 3.0) | 59.0 (stdev = 3.6) |

EXAMPLE 2

The effectiveness of the modified particles to adsorb odorous compounds was demonstrated. The particles were Snowtex-AK, which are colloidal silica nanoparticles coated with alumina and commercially available from Nissan Chemical America of Houston, Tex. The particles were modified with a transition metal as follows. Initially, 1 milliliter of a 10-millimolar hematoxylin dye solution was added to an equal volume of a 10-millimolar of copper chloride ($CuCl_2$). The solution immediately changed from a pale yellow to a deep blue, indicating the formation of a complex. To this complex was then added 1 millimeter of a 200-micromolar solution of the Snowtex-AK particles (approximately 20 wt. % solids). Thus, the ratio of copper-coordinated dye to the particles was 50:1. The solution rapidly changed in color as the second catechol group bonded to the alumina-coated particles.

The mixture was stirred at room temperature for 20 minutes, and then the solvent was removed under rotary evaporation. The dried particles (approximately 200 milligrams) were split into 2 portions, one of which was washed to remove any unbound dye and/or copper. No dye was observed in the washes. About 60 milligrams of each sample was then placed into a 100-microliter screwtop jar that contained two slices of freshly cut garlic. The caps were screwed shut, and the dried particles and odor were incubated at room temperature for 30 minutes. Qualitative comparison indicated that the samples formed with the dye reduced the odor to a much greater extent than a "no dye" control sample.

The solutions containing the dye were applied to a polyester/cotton blend (from a t-shirt). The polyester/cotton blend was subjected to 3 washes in hot water/detergent using a commercial washing machine. The intense coloration of the fabric from the dye complex was only marginally reduced by this process, indicating high durability of the coating. Three samples of the products were also tested for odor adsorption as described above. For comparative purposes, three samples were also tested that did not contain the dye. The results are shown below in Table 3 in terms of the average percentage of odorous compound removed for the three samples.

TABLE 3

Removal of Odorous Compounds

| Sample | Avg. % Ethyl Mercaptan Removed | Avg. % TEA Removed | Avg. % Isovaleraldehyde Removed |
|---|---|---|---|
| Control | 11.3 (stdev = 3.2) | 15.0 (stdev = 3.0) | 10.3 (stdev = 2.9) |
| Copper/ Snowtex-AK/ Hematoxylin | 57.0 (stdev = 6.1) | 59.3 (stdev = 6.0) | 60.3 (stdev = 2.1) |

EXAMPLE 3

Modified particles were formed as in Example 2, except that the ratio of copper-coordinated dye to the particles was 100:1. 10 milliliters of this solution was then placed into a 3500 MW cutoff dialysis bag and dialyzed overnight against 2 liters of distilled deionized water. Upon completion, there was only a small amount of dye that had diffused out of the dialysis bag, indicating almost complete chemisorption of the copper-dye complex onto the particles. The water was removed from this solution under rotary evaporation. The solution containing the dye were applied to a polyester/cotton blend (from a t-shirt). The polyester/cotton blend was subjected to 3 washes in hot water/detergent using a commercial washing machine. The intense coloration of the fabric from the dye complex was only marginally reduced by this process, indicating high durability of the coating.

EXAMPLE 4

The effectiveness of the modified particles to adsorb odorous compounds was demonstrated. The particles were Snowtex-AK, which are colloidal silica nanoparticles coated with alumina and commercially available from Nissan Chemical America of Houston, Tex. The particles were modified with a transition metal as follows. Initially, 1 milliliter of a 10-millimolar solution of EDTA was added to an equal volume of a 10-millimolar of copper chloride ($CuCl_2$). The solution immediately changed from a very pale blue color to a dark to medium blue color, indicating the formation of a complex. To this complex was then added 1 millimeter of a 200-micromolar solution of the Snowtex-AK particles (approximately 20 wt. % solids). Thus, the ratio of copper-coordinated dye to the particles was 50:1. The solution remained soluble and blue-colored.

The sample solution was then dialyzed to remove any unbound EDTA-copper complex. After 24 hours and two changes of the dialysate, 1 milliliter of the solution (still blue in color) was placed into a small glass vial that contained freshly cut garlic, and sealed at room temperature for 1 hour. A noticeable reduction in odor was observed. The solution was then placed onto a Scott® paper towel and allowed to dry. The garlic test was repeated. When applied to the paper towel and test, an even greater level of odor reduction was noted. Another Scott® paper towel applied with the sample solution was also placed in 2 millimeters of freshly collected pooled urine, and incubated overnight at 32° C. A dramatic reduction in urine odor was noted.

For comparison, the order of addition was reversed for one sample, i.e., the EDTA solution was first added to the Snowtex-AK particles before mixing with the copper chloride. For this sample, an immediate precipitation occurred, which hindered subsequent adsorption of copper ions.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for reducing odor, said method comprising:
    modifying particles having a positive zeta potential with a transition metal, wherein a bifunctional chelating agent complexes said transition metal to said particles, wherein said bifunctional chelating agent is a catechol that contains one or more iminodiacetic acid groups; and
    contacting said modified particles with an odorous compound, said transition metal providing one or more active sites for capturing said odorous compound.

2. A method as defined in claim 1, wherein said particles are formed from a material selected from the group consisting of silica, alumina, zirconia, magnesium oxide, titanium dioxide, iron oxide, zinc oxide, copper oxide, polystyrene, and combinations thereof.

3. A method as defined in claim 1, wherein said particles comprise alumina.

4. A method as defined in claim 3, wherein said particles comprise silica coated with alumina.

5. A method as defined in claim 1, wherein said particles have an average size of about 500 microns or less.

6. A method as defined in claim 1, wherein said particles have an average size of about 100 nanometers or less.

7. A method as defined in claim 1, wherein said particles have an average size of from about 4 to about 20 nanometers.

8. A method as defined in claim 1, wherein said particles have a surface area of from about 50 to about 1000 square meters per gram.

9. A method as defined in claim 1, wherein said transition metal is selected from the group consisting of scandium, titanium, vanadium, chromium, manganese, iron, cobalt, nickel, copper, zinc, silver, gold, and combinations thereof.

10. A method as defined in claim 1, wherein said particles have a zeta potential of about +20 millivolts or more.

11. A method as defined in claim 1, wherein said particles have a zeta potential of about +30 millivolts or more.

12. A method as defined in claim 1, wherein said particles have a zeta potential of about +40 millivolts or more.

13. A method as defined in claim 1, wherein said bifunctional chelating agent contains moieties selected from the group consisting of hydroxyl, carboxy, imino, amino, carbonyl, and combinations thereof.

14. A method as defined in claim 1, wherein said odorous compound is selected from the group consisting of mercaptans, ammonia, amines, sulfides, ketones, carboxylic acids, aldehydes, terpenoids, hexanol, heptanal, pyridine, and combinations thereof.

15. A method as defined in claim 1, further comprising applying said modified particles to a substrate.

16. A method as defined in claim 15, wherein said substrate comprises a nonwoven, woven, or paper web.

17. A substrate for reducing odor, said substrate being applied with particles coated with alumina that are modified with a transition metal, said particles having a positive zeta potential, wherein a bifunctional chelating agent complexes said transition metal to said particles, wherein said bifunctional chelating agent is a catechol that contains one or more iminodiacetic acid groups, wherein said transition metal provides one or more active sites for capturing an odorous compound.

18. A substrate as defined in claim 17, wherein said particles are formed from silica.

19. A substrate as defined in claim 17, wherein said particles have an average size of about 100 nanometers or less.

20. A substrate as defined in claim 17, wherein said particles have a surface area of from about 50 to about 1000 square meters per gram.

21. A substrate as defined in claim 17, wherein said transition metal is selected from the group consisting of scandium, titanium, vanadium, chromium, manganese, iron, cobalt, nickel, copper, zinc, silver, gold, and combinations thereof.

22. A substrate as defined in claim 17, wherein said particles have a zeta potential of about +20 millivolts or more.

23. A substrate as defined in claim 17, wherein said particles have a zeta potential of about +30 millivolts or more.

24. A substrate as defined in claim 17, wherein said particles have a zeta potential of about +40 millivolts or more.

25. A substrate as defined in claim 17, wherein the substrate comprises a nonwoven, woven, or paper web.

26. A substrate as defined in claim 17, wherein said modified particles are present at a solids add-on level of from about 0.001% to about 20%.

27. An absorbent article that comprises the substrate of claim 17.

28. An absorbent article as defined in claim 27, further comprising at least one liquid-transmissive layer and a liquid-absorbent core, wherein said substrate forms at least a portion of said liquid-transmissive layer, said liquid-absorbent core, or combinations thereof.

29. An absorbent article as defined in claim 28, wherein the absorbent article includes a liquid-transmissive liner, a liquid-transmissive surge layer, a liquid-absorbent core, and a vapor-permeable, liquid-impermeable outer cover, said substrate forming at least a portion of said liner, said surge layer, said absorbent core, said outer cover, or combinations thereof.

30. A paper product that comprises the substrate of claim 17.

31. A facemask that comprises the substrate of claim 17.

32. A substrate for reducing odor, said substrate being applied with particles coated with alumina that are modified with a transition metal, said particles having a positive zeta potential, wherein a bifunctional chelating agent complexes said transition metal to said particles, wherein said bifunctional chelating agent contains a dye, wherein said transition metal provides one or more active sites for capturing an odorous compound.

33. A substrate as defined in claim 32, wherein said particles are formed from silica.

34. A substrate as defined in claim 32, wherein said particles have an average size of about 100 nanometers or less.

35. A substrate as defined in claim 32, wherein said transition metal is selected from the group consisting of scandium, titanium, vanadium, chromium, manganese, iron, cobalt, nickel, copper, zinc, silver, gold, and combinations thereof.

36. A substrate as defined in claim 32, wherein said particles have a zeta potential of about +20 millivolts or more.

37. A substrate as defined in claim 32, wherein said dye includes an anthraquinone dye.

38. A substrate as defined in claim 32, wherein the substrate comprises a nonwoven, woven, or paper web.

39. A substrate as defined in claim 32, wherein said modified particles are present at a solids add-on level of from about 0.001% to about 20%.

* * * * *